(12) United States Patent
Geais

(10) Patent No.: US 11,141,281 B2
(45) Date of Patent: Oct. 12, 2021

(54) METHOD FOR CONSTRUCTING A RANGE OF HUMERAL COMPONENTS FOR SHOULDER JOINT PROSTHESES

(71) Applicant: MOVE-UP, Alixan (FR)

(72) Inventor: Laurent Geais, Romans (FR)

(73) Assignee: MOVE-UP, Alixan (FR)

( * ) Notice: Subject to any disclaimer, the term of this patent is extended or adjusted under 35 U.S.C. 154(b) by 187 days.

(21) Appl. No.: 16/440,530

(22) Filed: Jun. 13, 2019

(65) Prior Publication Data

US 2019/0290444 A1 Sep. 26, 2019

Related U.S. Application Data

(63) Continuation of application No. PCT/FR2017/053487, filed on Dec. 11, 2017.

(30) Foreign Application Priority Data

Dec. 13, 2016 (FR) ...................................... 1662380

(51) Int. Cl.
*A61F 2/40* (2006.01)
*A61B 34/10* (2016.01)
*A61F 2/30* (2006.01)

(52) U.S. Cl.
CPC ............ *A61F 2/4059* (2013.01); *A61B 34/10* (2016.02); *A61F 2/3094* (2013.01); *A61B 2034/108* (2016.02); *A61F 2002/30332* (2013.01); *A61F 2002/30616* (2013.01); *A61F 2002/30943* (2013.01); *A61F 2002/30952* (2013.01); *A61F 2002/4037* (2013.01)

(58) Field of Classification Search
CPC .. A61F 2/40; A61F 2/4059; A61F 2/30; A61F 2/3094; A61B 34/10
See application file for complete search history.

(56) References Cited

U.S. PATENT DOCUMENTS 5,725,592 A 3/1998 White et al.
9,020,788 B2 * 4/2015 Lang ......................... A61F 2/40
703/6

(Continued)

OTHER PUBLICATIONS

International Search Report for International Application PCT/FR2017/053487, dated May 2, 2018.

*Primary Examiner* — Christopher J Beccia
(74) *Attorney, Agent, or Firm* — Burris Law, PLLC

(57) ABSTRACT

A system and method for the field of humeral components for shoulder joint prostheses and, more specifically, to a method for constructing a range of humeral components intended to be inserted into the proximal region of the humerus during reconstructive shoulder surgery includes the following steps: obtaining a set (Evs) of statistical data relating to variables that can be used to characterise the geometry of a proximal humerus region from morphometric data (Dm) of proximal humerus regions belonging to a representative sample of a population; based on a statistical distribution, determining a set (G) of sizes forming the range of humeral components; for each of the sizes, determining a measurement (MiTn-n) for each of the variables, according to the set of statistical data; and for each of the sizes, producing a humeral component according to the measurement of each of the variables corresponding to the size.

15 Claims, 10 Drawing Sheets

(56) References Cited

U.S. PATENT DOCUMENTS

| | | |
|---|---|---|
| 2004/0143335 A1 | 7/2004 | Dews et al. |
| 2007/0191741 A1* | 8/2007 | Tsai ................... A61B 5/4528 600/587 |
| 2014/0081422 A1* | 3/2014 | Hugate ................ A61F 2/2814 623/32 |
| 2015/0250601 A1 | 9/2015 | Humphrey |
| 2016/0270854 A1* | 9/2016 | Chaoui ................ A61F 2/4081 |
| 2017/0071748 A1* | 3/2017 | Humphrey .......... A61F 2/30942 |

* cited by examiner

METHOD FOR CONSTRUCTING A RANGE OF HUMERAL COMPONENTS FOR SHOULDER JOINT PROSTHESES

CROSS-REFERENCE TO RELATED APPLICATIONS

This application is a continuation of International Application No. PCT/FR2017/053487, filed on Dec. 11, 2017, which claims priority to and the benefit of FR 16/62380 filed on Dec. 13, 2016. The disclosures of the above applications are incorporated herein by reference.

FIELD

The present disclosure relates to the field of shoulder joint prostheses, and more particularly to the field of short humeral components for shoulder joint prostheses.

BACKGROUND

The statements in this section merely provide background information related to the present disclosure and may not constitute prior art.

The present disclosure concerns in particular a method for constructing a range of humeral components for shoulder joint prostheses. The present disclosure applies to shoulder reconstruction surgeries.

It is particularly desirable for a joint prosthesis to allow restitution of the mobilities of the joint that it replaces.

In the particular case of a shoulder joint prosthesis, the various lever arms observed at the level of the replaced joint—that is to say the distances between the centers of rotation and the points of application of the forces at the level of the corresponding muscular insertions—must be able to be restored as accurately as possible. These distances are defined between the endocanalar shape of the humeral component of the prosthesis and the center of the joint surface.

In particular, in order to meet the objective of preserving the various lever arms, the humeral component, intended to be introduced into the proximal portion of the humerus, must have an endocanalar shape adapted to the largest possible number of morphotypes in the population.

Yet, the ranges of humeral components according to the prior art generally allow adapting only very partially to the various morphologies of patients, whose sizes vary greatly.

Furthermore, the time required to develop a range of humeral components according to known construction methods is still particularly considerable, because it is necessary to carry on calculations and design for each size of humoral components constituting the range. It is a long and complex iterative process, requiring a large marking time.

It is still particularly desirable for a humeral component to ensure an angular blocking in optimal rotation, in order to avoid loosening, once disposed in the proximal portion of the humerus.

Yet, the rotational stability of the humeral components according to the prior art is still to be improved, in particular for short humeral components—that is to say, typically with a length smaller than 100 mm.

The state of the art can also be illustrated by the teaching of the documents U.S. Pat. No. 5,725,592 and US 2015/0250601 which disclose methods for constructing ranges of humeral components intended to be introduced into the proximal portion of the humerus during a shoulder reconstruction surgery, the disclosures of which are incorporated herein in their entirety by reference.

SUMMARY

One of the objects of the teachings disclosed herein is to enable the design of a range of humeral components adapted to enable the restitution of the mobilities of the joint they replace, in particular the various lever arms observed at the level of the replaced joint.

One of the objects of the teachings disclosed herein is to enable the design of a range of humeral components having an endocanalar shape adapted to the largest possible number of morphotypes in the population.

One of the objects of the teachings disclosed herein is to reduce the time required to develop a range of humeral components.

One of the objects of the teachings disclosed herein is to enable the design of a range of short humeral components adapted to ensure an angular locking in optimal rotation, in order to avoid loosening, once disposed in the proximal portion of the humerus.

One or more of these objects are addressed by the method disclosed herein.

More particularly, according to a first aspect, a method for constructing a range of humeral components intended to be introduced into the proximal portion of the humerus during a shoulder reconstruction surgery includes the following steps of:

obtaining a set of statistical data relating to variables adapted to enable the characterization of the geometry of a proximal portion of the humerus, from morphometric data of proximal portions of the humerus belonging to a representative sample of a population;

determining, from a statistical distribution, a set of sizes composing the range of humeral components;

for each of said sizes, determining a measurement for each of the variables, according to the set of statistical data;

for each of said sizes, producing a humeral component according to the measurement of each of the variables corresponding to said size.

By implementing the method according to the disclosure, it is possible to control the time required for the development of a range of humeral components.

Furthermore, it is also possible to optimize the management of the range, by means of the statistical distribution, and thus define an optimal stock size at the production level, but also in clinics and hospitals.

Furthermore, since the range is optimized according to information relating to a representative sample of a population, the range offered to the surgeon allows assisting in the choice of an appropriate humeral component.

Variables adapted to enable the characterization of the geometry of a proximal portion of the humerus comprise, for example, one or more of the following variables:
  a medial offset,
  a posterior offset,
  a mechanical offset,
  a retrotorsion/bi-epicondylar,
  a retrotorsion/posterior,
  a cervico-diaphysial angle,
  a diameter of the joint surface,
  a thickness of the joint surface,
  an anteroposterior and mediolateral bulk of each of the transverse sections of the humeral component.

The statistical distribution can be determined, for each of the variables, according to the average value and the standard deviation, relating to said variable, in the set of statistical data.

Advantageously, each humeral component of the range has a length substantially smaller than 100 mm.

The method may then include a step of obtaining at least one reference value of a torsion torque likely to cause loosening of a humeral component installed in a proximal portion of the humerus, and in which, the measurement for each variable, for each of said sizes, is determined according to the set of statistical data and according to said at least one reference value.

For each of said sizes, the measurement for each of the variables, according to the set of statistical data, can be determined by:

obtaining a three-dimensional model of a humeral component including sections distributed in different planes, each section being defined by a set of geometric parameters;

determining, for each of the sections, the set of corresponding geometrical parameters, according to the set of statistical data relating to the variables able to enable the characterization of the geometry of a proximal portion of the humerus;

determining, for each of said geometrical parameters, by means of an interpolation function, the values of said parameter between each section.

For each of the sections, the set of corresponding geometrical parameters can be determined according to the set of statistical data relating to the variables adapted to enable the characterization of the geometry of a proximal portion of the humerus, and according to said at least one reference value.

For example, the sections have a substantially octagonal shape, each section being provided with fillets with configurable radii, the values of the configurable radii being selected according to said at least one reference value.

The octagonal sections thus allow passing from a stabilizing section—that is to say with a very small radius—into a distal section with a substantially quasi-circular shape so as not to come into contact with the diaphysis.

Thus, it is possible to considerably reduce the risks associated with the contacts of the humeral component with the diaphysis, namely the problems of stress deflection problems, more commonly referred to as "stress-shielding", and the occurrence of pains at the tip of the pin.

With the construction method according to the present disclosure, it is possible to construct a range of humeral components intended to be introduced into the proximal portion of the humerus during a shoulder reconstruction surgery, each humeral component being constructed according to the construction method according to the first aspect.

According to a second aspect, the disclosure relates to a system for constructing a range of humeral components intended to be introduced into the proximal portion of the humerus during a shoulder reconstruction surgery.

The system is particularly suitable for implementing the method according to the first aspect. The system includes:

a database including a set of statistical data relating to variables adapted to enable the characterization of the geometry of a proximal portion of a humerus, from morphometric data of proximal portions of the humerus belonging to a representative sample of a population;

a configurator adapted to:

determine, from a statistical distribution, a set of sizes composing the range of humeral components;

for each of said sizes, determine a measurement for each of the variables, according to the set of statistical data;

a production tool configured to produce, for each of said sizes, a humeral component according to the measurement of each of the variables corresponding to said size.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
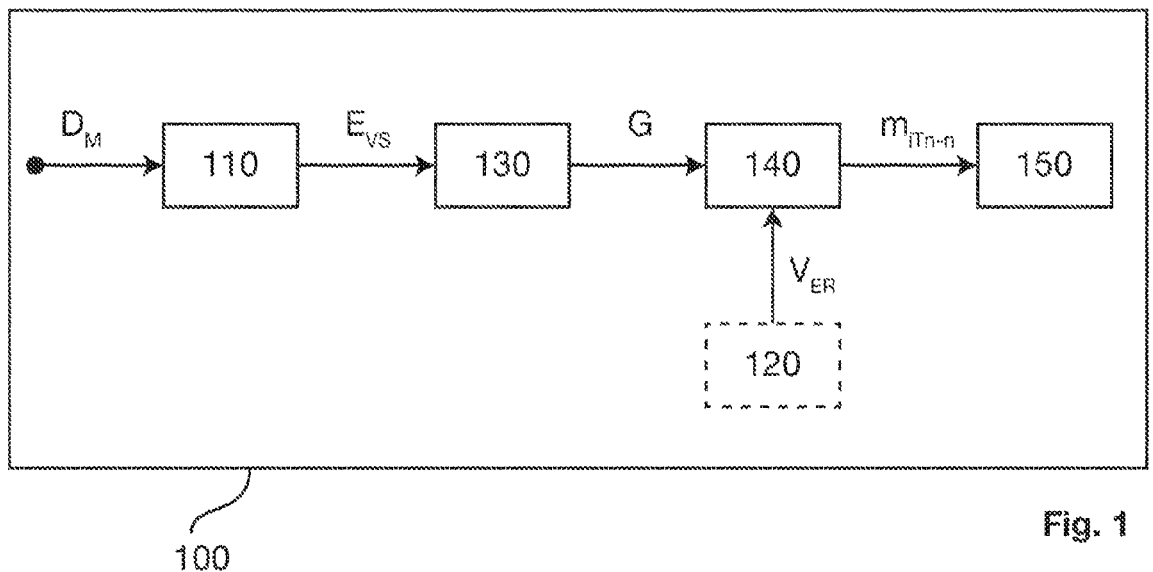
FIG. 1 is a flowchart illustrating one form of a construction method, according to the teachings of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 17:
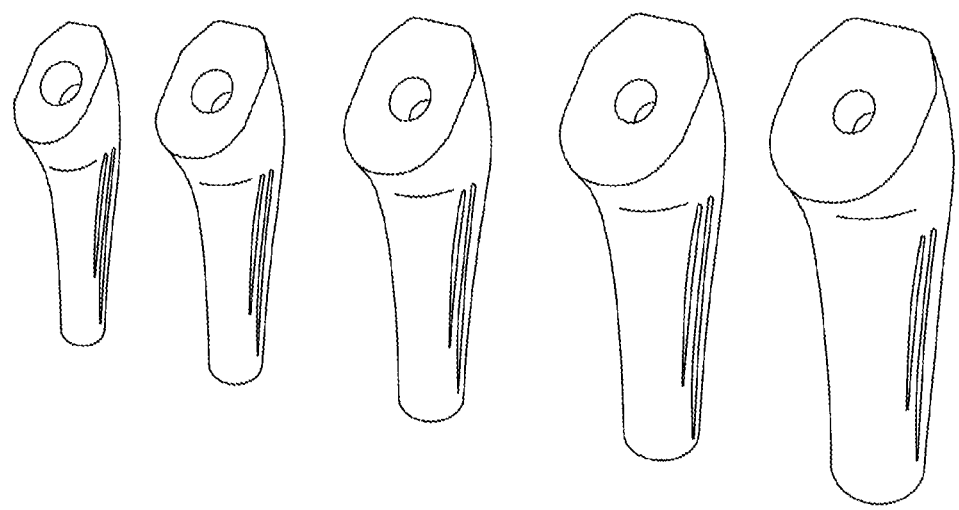
FIG. 17 is a three-dimensional view representing a range of humeral components for prostheses, obtained by way of the method according to the teachings of the present disclosure.

FIG. 1 illustrates a construction method 100, for constructing a range of humeral components for prostheses, in particular the range shown in FIG. 17. The humeral components of the range are intended for a shoulder reconstruction surgery.

Each humeral component of the range includes an endocanalar portion intended to be introduced into the proximal portion of the humerus. The range of humeral components includes a plurality of short humeral components—that is to say, typically having a length smaller than 100 mm—shown in FIG. 17. It is indeed advantageous to provide short humeral components because it is thus possible to facilitate the revision surgeries.

The various endocanalar shapes of the humeral components of the range obtained by the implementation of the method provide the surgeons with the possibility of choosing a humeral component in said range, with a high probability that said humeral component is adapted to the morphology of the proximal portion of the humerus of the patient to operate. The recovery is typically 95% of the population for a range drawn with a size 1 having the parameters of $\mu-2\sigma$ and a size 9 having the parameters of $\mu+2\sigma$, as detailed hereinafter in the description.

The method includes a first step 110 during which morphometric data $D_M$, corresponding to variables $V_n$ adapted to characterize proximal portions of the humerus belonging to a sample E representative of a population, are collected.

At the end of step 110, a set $E_{vs}$ of statistical data, relating to the variables $V_n$, is obtained.

Advantageously, the method includes an optional second step 120, during which reference values $V_{Er}$ of torsion torques likely to cause loosening of humeral components, installed in proximal portions of the humerus belonging to a sample E' representative of a population are obtained.

The method includes a third step 130 during which, from a statistical distribution $D_T$, a set G of sizes $T_n$ composing the range of humeral components is determined.

The method includes a fourth step 140 during which, for each size $T_n$ of the set G, a measurement $m_{iTn-n}$ is determined, for each variable $V_n$, according to the set $E_{vs}$ of statistical data, and, advantageously, according to the reference values $V_{Er}$.

The method includes a fifth step 150 during which, the range of humeral components is obtained, by producing, for each size $T_n$ of the set G, a humeral component according to the measurements $m_{iTn-n}$ relating to the variables $V_n$ corresponding to said size $T_n$.

Figure 2:
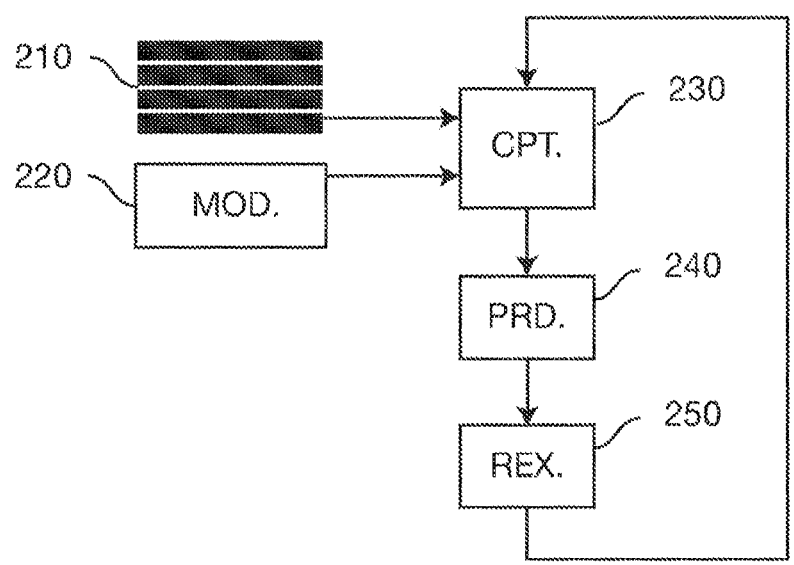
FIG. 2 is a diagram of one form of a construction system, according to the teachings of the present disclosure.
Figure 3:
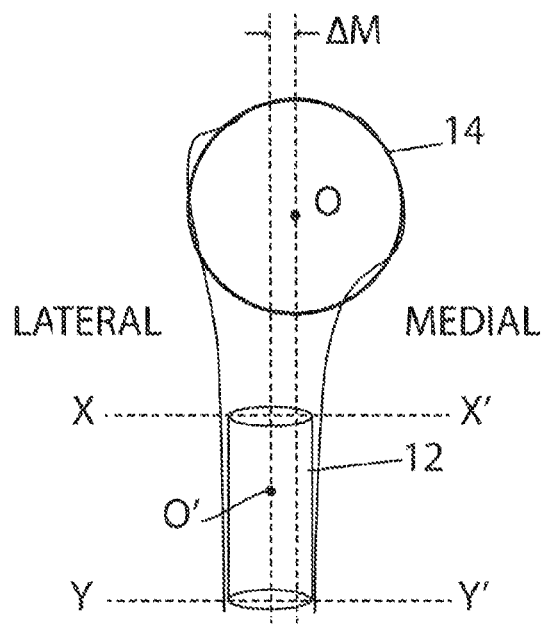
FIG. 3 is a schematic view of a metaphyseal cylinder and epiphysis sphere model, according to a reference construction, superimposed on an anatomical view of a typical humerus, in accordance with the teachings of the present disclosure.

Referring to FIG. 2, which schematically represents a construction system, according to one form. The system is in particular adapted to implement the construction method 100, to construct a range of humeral components for prostheses.

The system allows facilitating the steps of designing the range of humeral components, by providing in particular the possibility of modifying and evaluating the geometry of each humeral component designed according to the morphometric data and the experience of surgeons.

The system includes a database 210 including the morphometric data $D_M$, corresponding to the variables $V_n$ adapted to characterize proximal portions of the humerus belonging to the sample E.

The system also includes a model 220 adapted to describe, for each size $T_n$ of the set G, the measurements $m_{iTn-n}$, for each variable $V_n$, according to the set $E_{vs}$ of statistical data, and, advantageously, according to the reference values $V_{Er}$.

The system includes a configurator 230, coupled to the database 210 and to the model 220, and adapted to define, for each size $T_n$ of the set G, a humeral component according to the measurements $m_{iTn-n}$ relating to the variables $V_n$ corresponding to said size $T_n$.

The configurator 230 may advantageously be coupled to a computer-aided design software, in order to allow, for example, automatically simulating the humeral components of the set G, according to the available morphometric data and laws.

The system includes a production tool 240, coupled to the configurator 230, configured to produce, for each size $T_n$ of the set G, a humeral component according to the measurements $m_{iTn-n}$ relating to the variables $V_n$ corresponding to said size $T_n$.

The system advantageously includes a tool for taking into account feedbacks 250 to collect new sets of statistical data, and coupled to the configurator 230 so as to allow the latter to take into account said new sets of statistical data.

Referring now to FIGS. 3 to 6, there is represented a reference construction for a proximal portion of a humerus. A reference construction for a proximal portion of the humerus is a geometric model comprising geometric objects, characterized by a set of variables whose values allow describing geometries of proximal portions of the humerus.

More particularly, in FIGS. 2 to 5, a model of metaphyseal cylinder 12 and epiphysis sphere 14 is represented.

Figure 6:
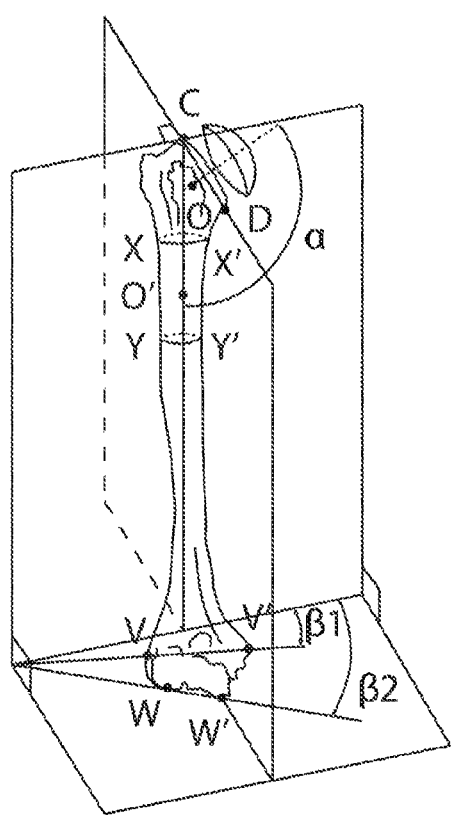
FIG. 6 is a schematic view representing, on a general anatomical view of a typical humerus, variables relating to said humerus, in accordance with the teachings of the present disclosure.

In this reference construction, the metaphyseal cylinder 12 is represented by a least squares cylinder, typically comprised between the planes XX' and YY', orthogonal to the diaphyseal axis of the humerus, and substantially distant respectively by 65 mm and by 105 mm, relative to the top of the joint surface C—also called Hinge point, and noted C in FIG. 6.

The epiphysis sphere 14 is represented by a least squares sphere passing through the points palpated on the joint surface of the epiphysis sphere of the humerus 10.

Figure 4:
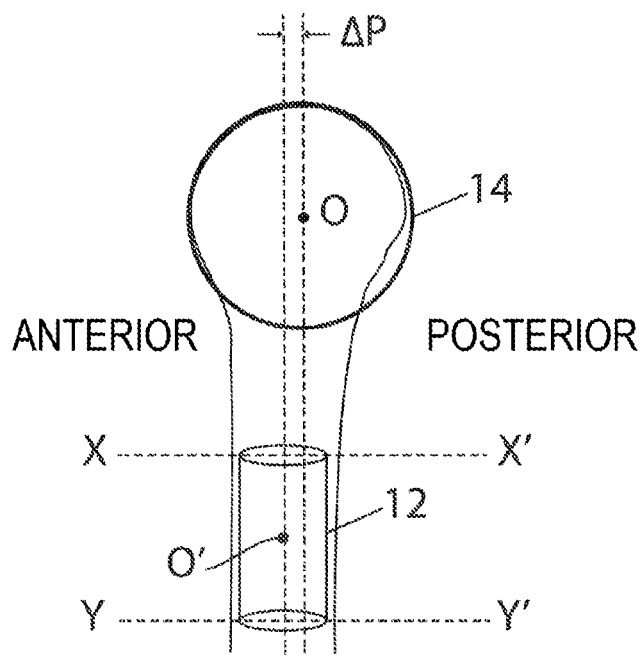
FIG. 4 is a schematic view of the metaphyseal cylinder and epiphysis sphere model, according to the reference construction, in accordance with the teachings of the present disclosure.
Figure 5:
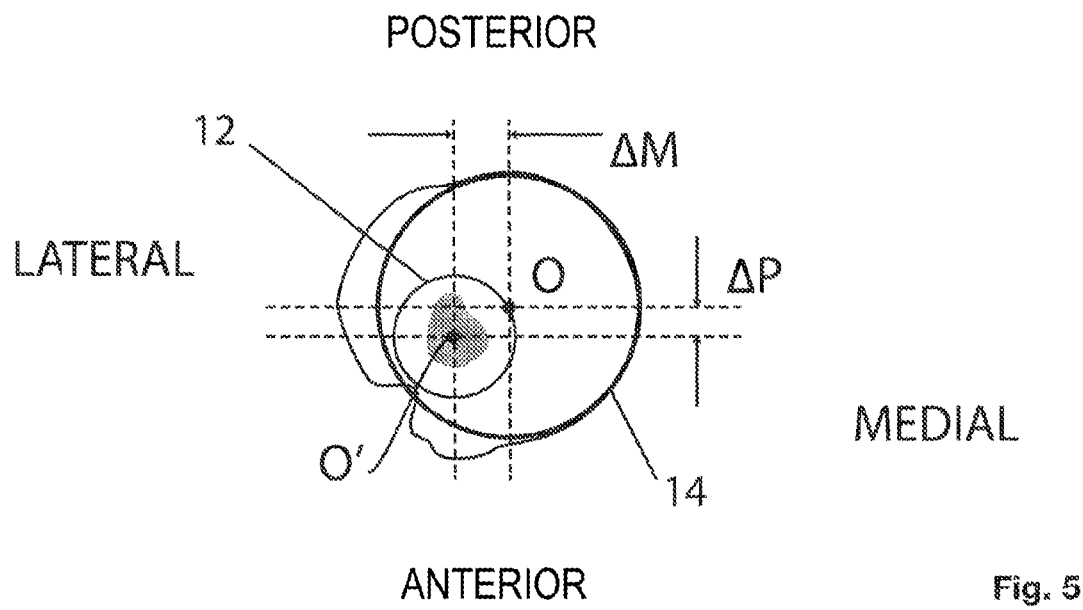
FIG. 5 is a schematic view representing, in a detailed anatomical view of a typical epiphysis sphere, variables relating to said epiphysis sphere, in accordance with the teachings of the present disclosure.

In FIGS. 4 and 5, variables relating to the metaphyseal cylinder 12 and the epiphysis sphere 14 are also represented.

In FIGS. 3 to 6, more particularly, are represented:

the medial offset ΔM, corresponding to the distance between the center of the humeral head—that is to say, the center of the least squares sphere—and the diaphyseal axis projected in the frontal plane;

the posterior offset ΔP, that is to say the distance between the center of the humeral head—that is to say the center of the least squares sphere—and the diaphyseal axis projected in the sagittal plane;

the mechanical offset $O_{MC}$, that is to say the distance between the center of the humeral head—that is to say the center of the least squares sphere—and the diaphyseal axis; the mechanical offset $O_{MC}$ can in particular be determined from the following mathematical expression:

$$O_{MC} = \sqrt{O_{MD}^2 + O_P^2}$$

the retrotorsion/bi-epicondylar $\beta_1$, that is to say the angle between the projection in the axial plane of the neck of the humerus and the bi-epicondylar line;

the retrotorsion/posterior $\beta_2$, that is to say the angle between the axis of the neck of the humerus and the two most posterior points of the distal joint surface of the humerus;

the cervico-diaphyseal angle α between the diaphyseal axis of the humerus and the normal axis OO';

the diameter $D_{SA}$ of the joint surface, namely the distance between the point C and the point D;

the thickness $E_{SA}$ of the joint surface.

Also, according to the previously-described reference construction example, the variables V(n) of the set EVS of statistical data considered are therefore the following ones:

the medial offset $O_{MD}$,
the posterior offset $O_P$,
the mechanical offset $O_{MC}$,
the retrotorsion/bi-epicondylar $\beta_1$,
the retrotorsion/posterior $\beta_2$,
the cervico-diaphyseal angle α,
the diameter $D_{SA}$ of the joint surface,
the thickness $E_{SA}$ of the joint surface.

The set $E_{VS}$ of statistical data, relating to morphological variables $V_n$ of proximal portions of the humerus belonging to the sample E, is thus determined, for said variables.

In one form, the set $E_{VS}$ of statistical data, relating to morphological variables $V_n$ of proximal portions of the humerus belonging to the sample E, is thus determined in particular from information, for example comprised in a database, grouping together values obtained for said variables $V_n$ during statistical studies.

Figure 7:
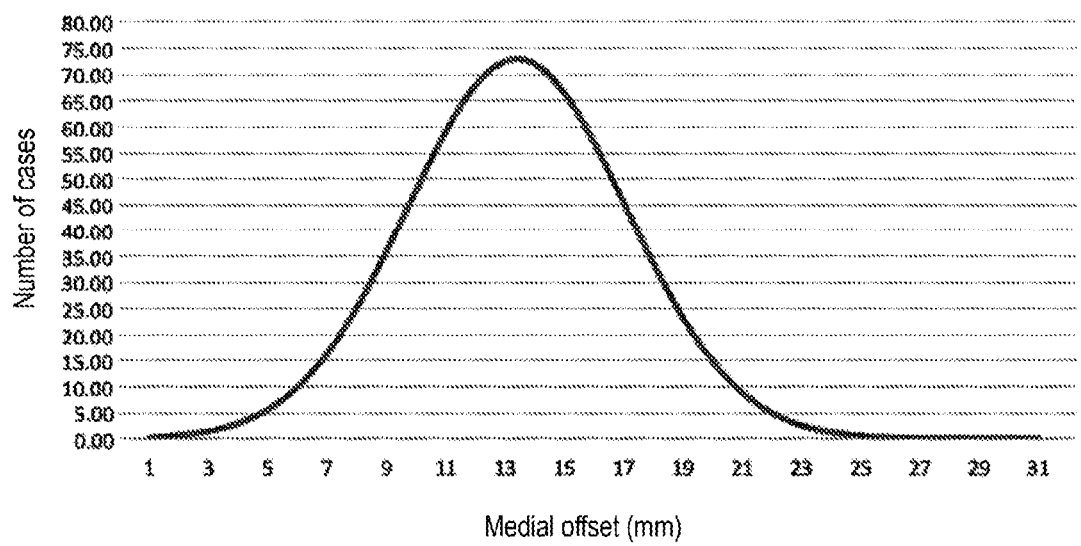
FIG. 7 is a diagram representing the number of people, in a population sample, corresponding to different values in mm of medial offset from statistical data on a population sample, in accordance with the teachings of the present disclosure.

Thus, the diagram illustrated in FIG. 7, representing the number of persons corresponding to different values in mm of medial offset $O_{MD}$ can be obtained from statistical data on the sample E, grouped together in a database.

During the optional second step 120, during which reference values $V_{Er}$ of torsion torques likely to cause loosening of humeral components, installed in proximal portions of the humerus, are determined.

Figure 8:
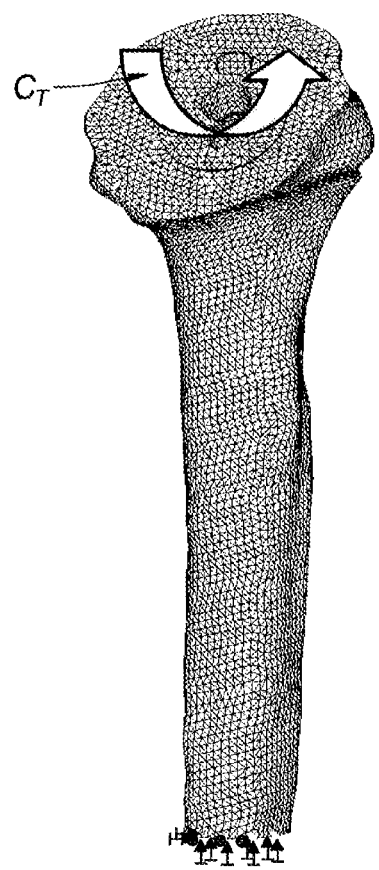
FIG. 8 is a schematic three-dimensional view, derived from a finite element simulation, on which is represented the torsion torque likely to cause loosening of the humeral component when the latter is implanted in a humerus, in accordance with the teachings of the present disclosure.

FIG. 8 represents a schematic three-dimensional view, derived from a finite element simulation, on which is represented a torsion torque $C_T$ likely to cause loosening of said humeral component when the latter is implanted in a humerus.

These data can also be obtained, experimentally, using a torque wrench so as to determine said reference values on the torsion torques likely to cause loosening of a humeral component implanted in the proximal portion of a humerus.

During the third step 130, the set G of sizes $T_{(n)}$, comprised in the range of humeral components, is determined, according to the set $E_{VS}$ of statistical data, from the statistical distribution $D_T$.

A size is an arbitrary value referring to a set of values for the different variables $V_n$, the diaphyseal dimensions being predominant.

In one form, the statistical distribution $D_T$ is determined, for each of the variables $V_n$, according to the average value M and to the standard deviation σ, relating to said variable $V_n$, in the set of statistical data for the sample E.

Thus, for each morphological variable $V_n$ for the sample E, for a range including 5 different sizes, the statistical distribution DT may be as follows:

| Size 1 | average value M − 2 × standard deviation σ |
| Size 3 | average value M − 1 × standard deviation σ |
| Size 5 | average value M |
| Size 7 | average value M + 1 × standard deviation σ |
| Size 9 | average value M + 2 × standard deviation σ |

The following table groups together the average values and the standard deviations according to the previously-described statistical distribution DT, for each morphological variable $V_n$ for the sample E, obtained from statistical data collected from medical studies and tests:

|  | M | σ | M − 2 × σ | M + 2 × σ |
|---|---|---|---|---|
| medial offset $O_{MD}$ | 6.2 mm | 1.9 mm | 2.4 mm | 10.0 mm |
| posterior offset $O_P$ | 1.7 mm | 1.7 mm | −1.7 mm | 5.1 mm |
| mechanical offset $O_{MC}$ | 6.4 mm | 2.5 mm | 2.9 mm | 11.2 mm |
| retrotorsion/bi-epicondylar $\beta_1$ | 17.9° | 13.7° | −9.5° | 45.3° |
| retrotorsion/posterior $\beta_2$ | 23° | 12.5° | −2° | 48° |
| cervico-diaphyseal angle α | 134.2° | 4.9° | 123.8° | 144.6° |
| diameter $D_{SA}$ | 44.2 mm | 4.0 mm | 36.2 mm | 52.2 mm |
| thickness $E_{SA}$ | 16.4 mm | 1.7 mm | 13.0 mm | 19.8 mm |

Referring now to FIGS. 12 to 15, in which, in one form, a three-dimensional model of a humeral component for a joint prosthesis is represented.

The model includes sections $S_n$ distributed in different planes $P_n$. In the example represented in FIGS. 11 to 14, nine sections $S_1 \ldots S_9$ are distributed in parallel planes $P_1 \ldots P_9$ orthogonal to the vertical axis XX'. The sections $S_1 \ldots S_9$ are spaced apart, in pairs, by a constant distance, proportional to the total length of the humeral component. Six sections $S_{10} \ldots S_{11}$ are distributed in planes $P_{10} \ldots P_{15}$. The plane $P_{10}$ is inclined according to an angle $\alpha_{10}$ with respect to the plane $P_9$. The plane $P_{11}$ is inclined according to an angle $\alpha_{11}$ with respect to the plane $P_{10}$. The plane $P_{12}$ is inclined according to an angle $\alpha_{12}$ with respect to the plane $P_{11}$. The plane $P_{13}$ is inclined according to an angle $\alpha_{13}$ with respect to the plane $P_{12}$. The plane $P_{14}$ is inclined at according to an angle $\alpha_{14}$ with respect to the plane $P_{13}$. The plane $P_{15}$ is inclined according to an angle $\alpha_{15}$ with respect to the plane $P_{14}$.

Figure 13:
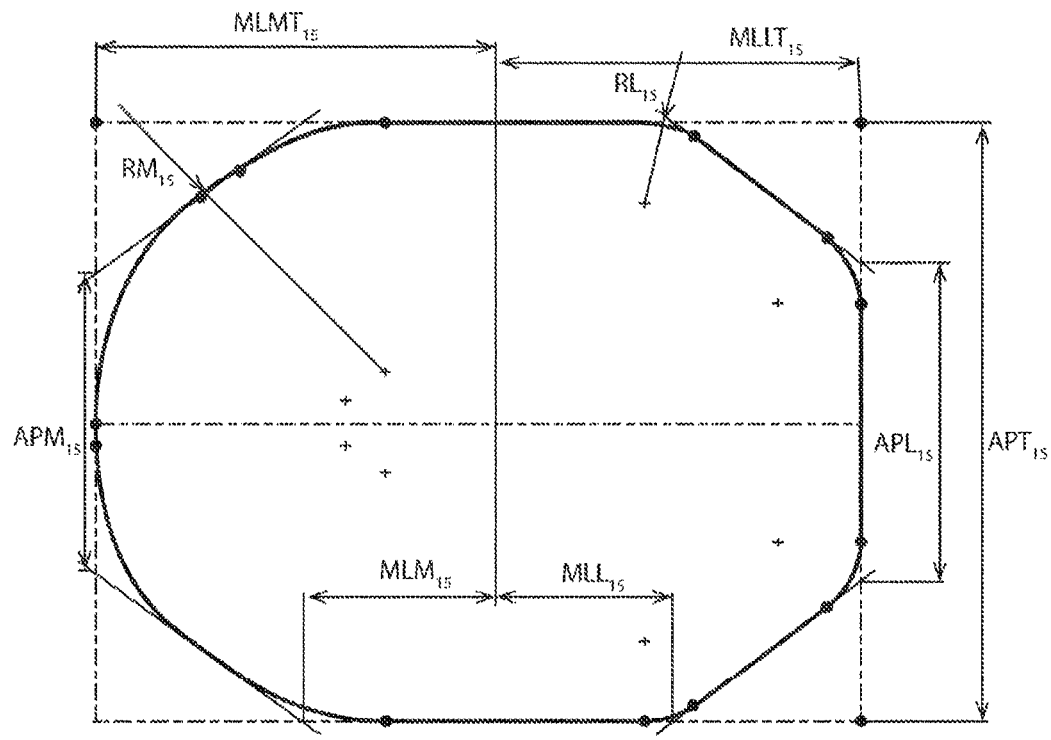
FIG. 13 is a diagram, representing a proximal section of the three-dimensional model of a humeral component for a joint prosthesis, in accordance with the teachings of the present disclosure.
Figure 14:
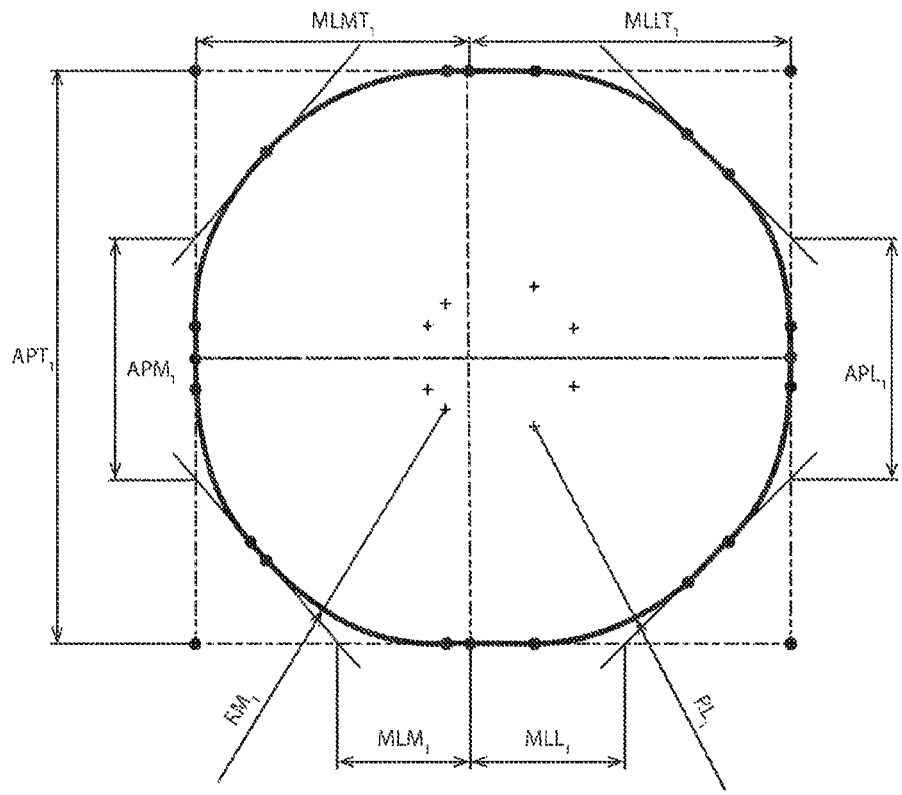
FIG. 14 is a diagram representing a distal section of the three-dimensional model of a humeral component for a joint prosthesis (measurements expressed in mm), in accordance with the teachings of the present disclosure.
Figure 15:
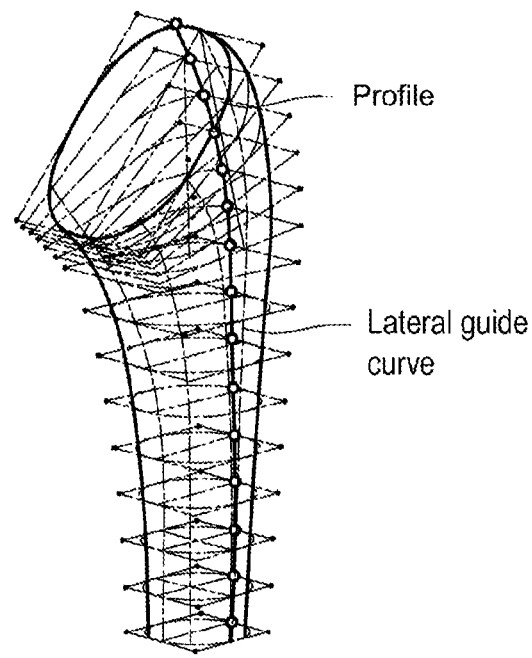
FIG. 15 is a diagram representing the distribution and the relative positioning of the sections of the three-dimensional model of a humeral component for a joint prosthesis, in accordance with the teachings of the present disclosure.

In one form, all of the angles $\alpha_{10 \ldots 15}$ are substantially equal. The section $S_{15}$ is represented in FIG. 13, the section $S_1$, in FIG. 14. The sections $S_n$ have a substantially octagonal shape, provided with configurable fillets. Each section $S_n$ can be described by a set of parameters $P_{Sn}$:
- a lateral radius $RL_n$,
- a medial radius $RM_n$,
- a lateral distance $MLM_n$,
- a total lateral distance $MLMT_n$,
- a medial distance $MLL_n$,
- a total median distance $MLLT_n$,
- a lateral distance $APL_n$,
- a medial distance $APM_n$,
- a total distance $APT_n$.

Also, for each size $T_{(n)}$ of the set G, the set of parameters $P_{Sn}$ is determined, for each of the sections $S_n$, according to the set $E_{VS}$ of statistical data. Then, for each parameter $P_{Sn}$ describing the sections $S_n$, the variations of the value of said parameter between each plane $P_n$ are interpolated.

Figure 9:
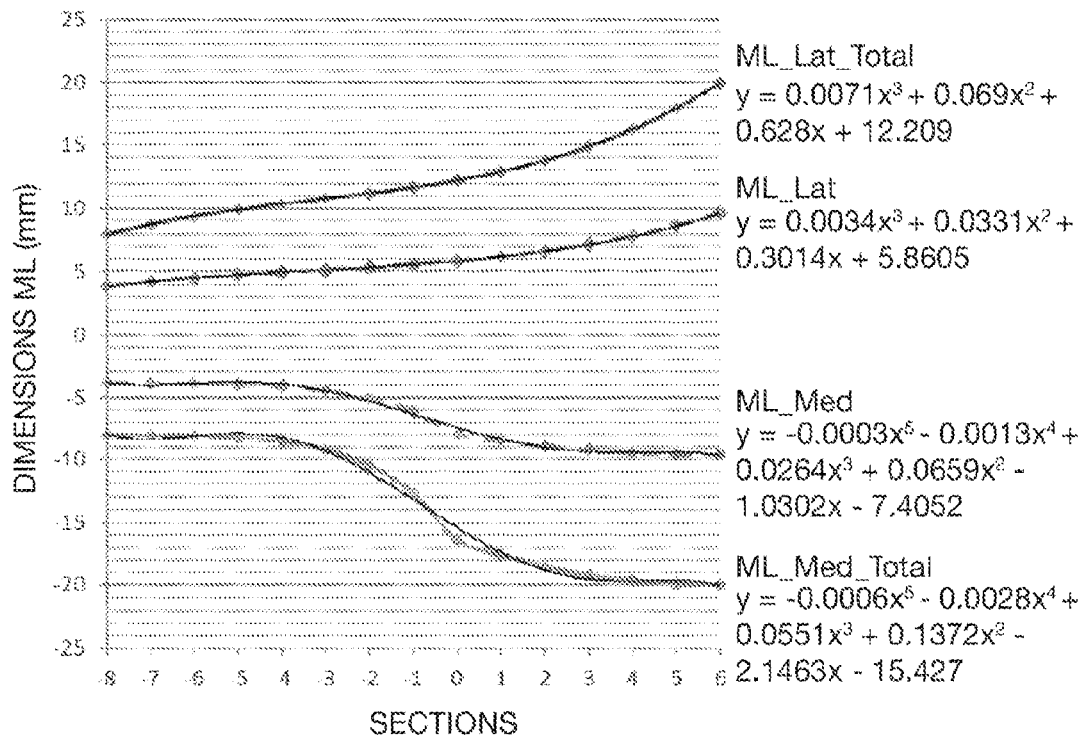
FIG. 9 is a diagram representing the interpolation functions for the following parameters: medial width ML_Med, lateral width ML_Lat, total medial width ML_Med_Total and total lateral width ML_Lat Total, in accordance with the teachings of the present disclosure.
Figure 10:
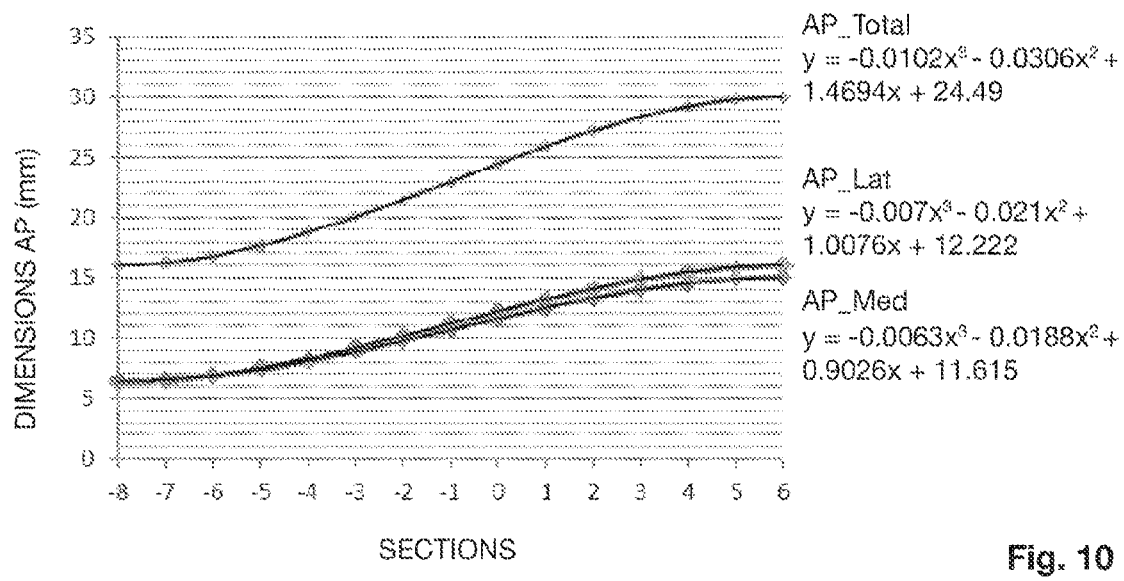
FIG. 10 is a diagram representing the interpolation functions for the following parameters: medial thickness AP_Med, lateral thickness AP_Lat and total thickness AP_Total, in accordance with the teachings of the present disclosure.
Figure 11:
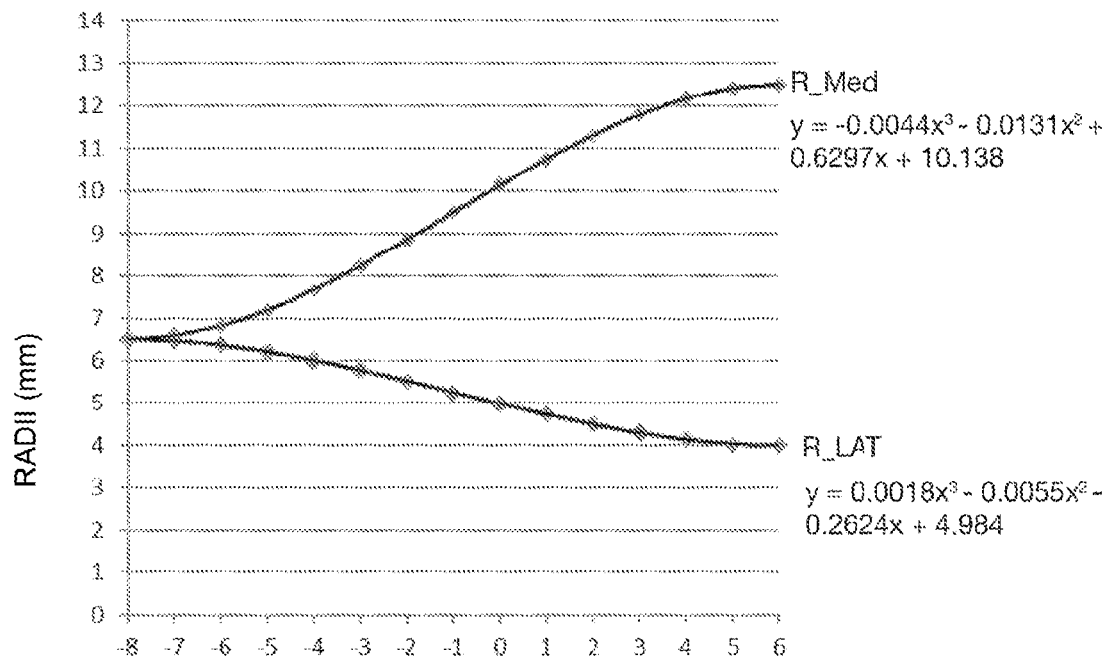
FIG. 11 is a diagram representing the interpolation functions for the following parameters: medial radius of the octagons R_Med and lateral radius of the octagons R_Lat, in accordance with the teachings of the present disclosure.
Figure 12:
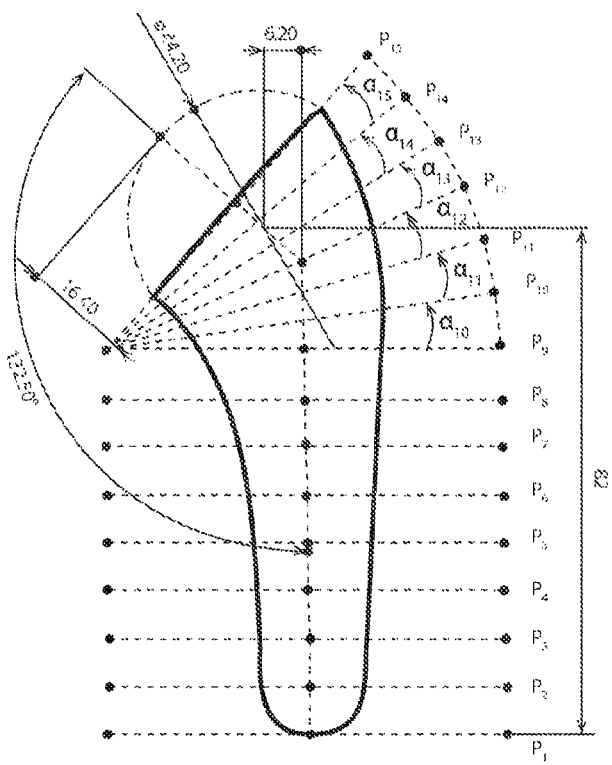
FIG. 12 is a diagram representing a three-dimensional model of a humeral component for a joint prosthesis (measurements expressed in mm), in accordance with the teachings of the present disclosure.

FIGS. 9 to 11 represent various interpolation functions $F_{PSn}$ specific to the different parameters $P_{Sn}$, for the size 5. The interpolation functions $F_{PSn}$ are typically $3^{rd}$ degree interpolation functions (thus with 2 inflection points).

In an advantageous form, for each size $T_{(n)}$ of the set G, the set of parameters $P_{Sn}$ is determined, for each of the sections $S_n$, according to the set $E_{VS}$ of statistical data and according to the reference values $V_{Er}$ of torsion torques likely to cause loosening of humeral components, determined during the second step 120.

More particularly, the lateral radius $RL_n$ and the medial radius $RM_n$ for each of the sections $S_n$ can be determined according to the reference values $V_{Er}$ of the torsion torque forces likely to cause loosening of humeral components.

Thus, the values of the lateral radius $RL_n$ and of the medial radius $RM_n$ for each of the sections $S_n$ are for example determined according to the reference values $V_{Er}$ and therefore according to the rotational stability need:

the smaller the value of the lateral radius $RL_n$ and/or of the medial radius $RM_n$, the greater said rotational stability will be, which is desirable for the proximal area of the humeral component;

the larger the value of the lateral radius $RL_n$ and/or of the medial radius $RM_n$, the lower the rotational stability will be, which is desirable for the distal area of the humeral component so as to facilitate insertion into the humerus and to limit stress deflection problems, more commonly referred to as "stress-shielding".

The range of humeral components is obtained by producing, for each size $T_{(n)}$ of the set G, a humeral component according to the corresponding model obtained, as previously described.

After having implemented the construction method, we thus obtain the range of short humeral components adapted to the morphologies of the patients, the range of humeral components allowing the surgeons to have, for each patient, an optimized short humeral component.

Figure 16A:
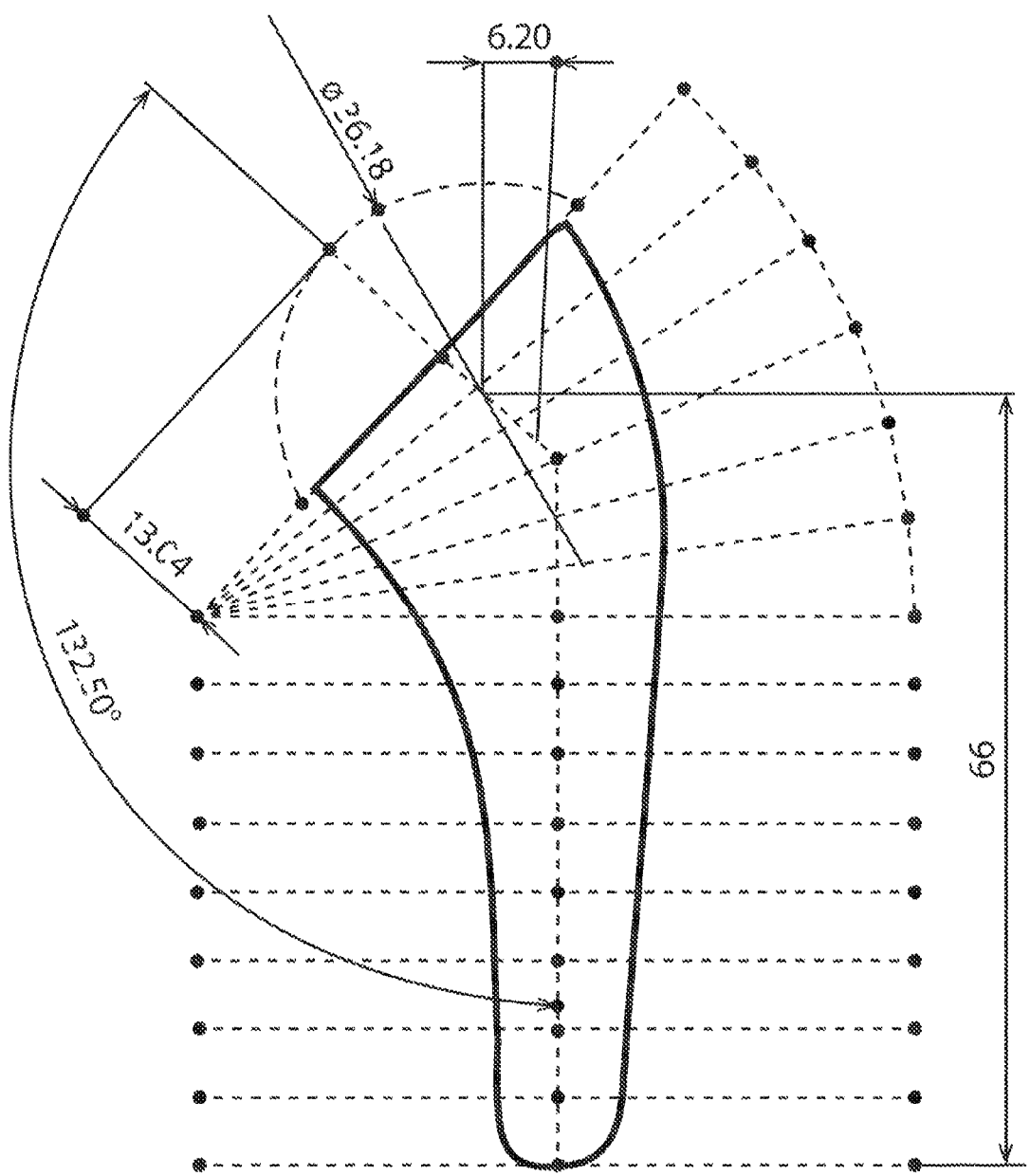
FIG. 16a is a three-dimensional view showing a humoral component of size 1, obtained by way of the method according to the teachings of the present disclosure.
Figure 16B:
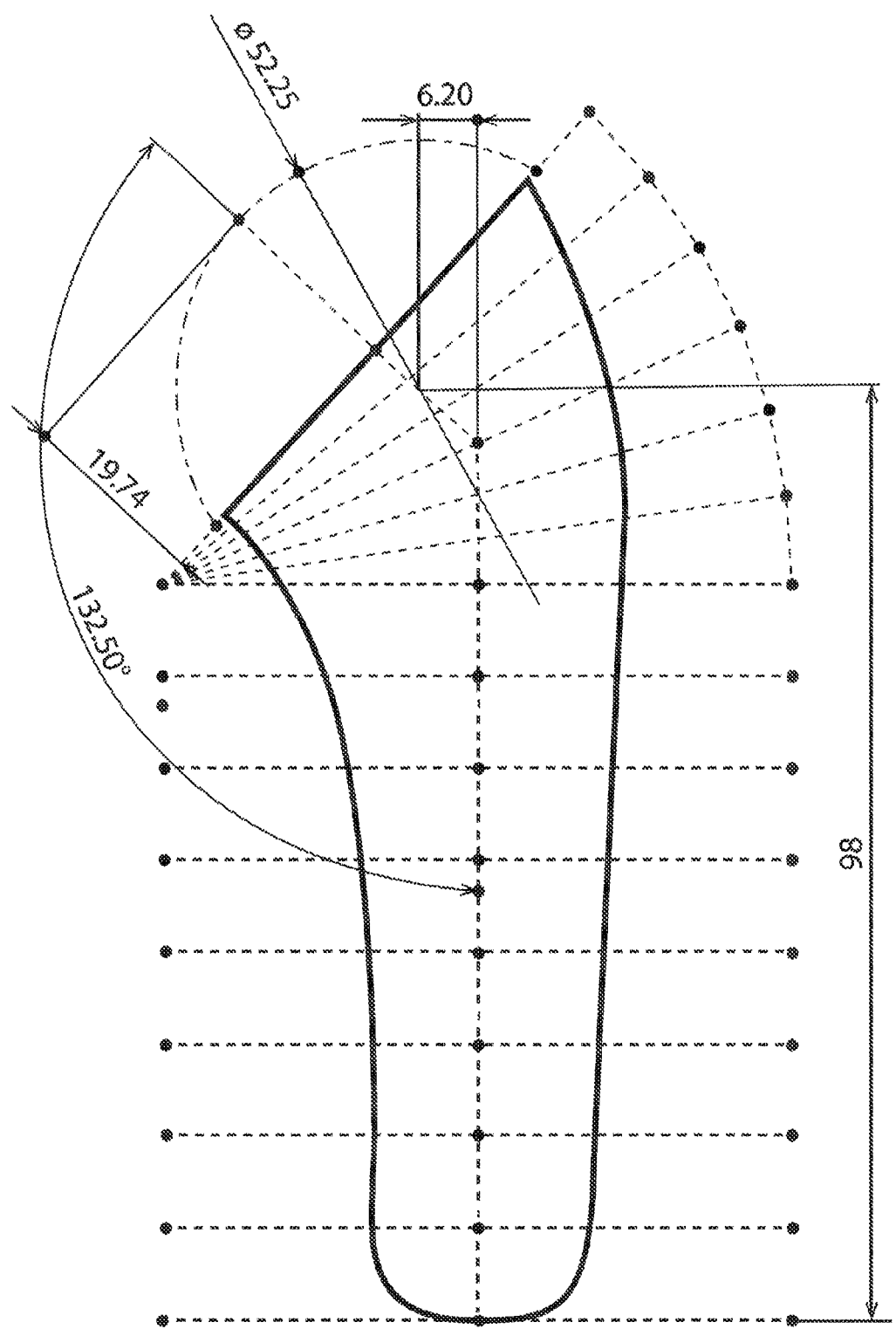
FIG. 16b is a three-dimensional view showing a humoral component of size 9, obtained by way of the method according to the teachings of the present disclosure.

FIG. 16a shows, in particular, an example of a humoral component of size 1 (measurements expressed in mm) obtained by way of the method disclosed herein. FIG. 16b shows, in particular, an example of a humoral component of size 9 (measurements expressed in mm) obtained by way of the method disclosed herein.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, manufacturing technology, and testing capability.

The description of the disclosure is merely exemplary in nature and, thus, variations that do not depart from the substance of the disclosure are intended to be within the scope of the disclosure. Such variations are not to be regarded as a departure from the spirit and scope of the disclosure.

As used herein, the phrase at least one of A, B, and C should be construed to mean a logical (A OR B OR C), using a non-exclusive logical OR, and should not be construed to mean "at least one of A, at least one of B, and at least one of C."

What is claimed is:

1. A method for constructing a range of humeral components that are configured to be introduced into the proximal portion of the humerus during a shoulder reconstruction surgery, the method comprises:
    obtaining a set of statistical data relating to variables adapted to enable the characterization of a geometry of a humerus proximal portion, from morphometric data of humerus proximal portions belonging to a representative sample of a population;
    determining, from a statistical distribution, a set of sizes composing the range of humeral components;
    for each of the sizes, determining a measurement for each of the variables, according to the set of statistical data; and
    for each of the sizes, producing a humeral component according to the measurement of each of the variables corresponding to the size.

2. The method according to claim 1, wherein the variables adapted to enable the characterization of the geometry of a humerus proximal portion comprise one or more of the following variables: a medial offset, a posterior offset, a mechanical offset, a retrotorsion/bi-epicondylar, a retrotorsion/posterior, a cervico-diaphysial angle, a diameter of the joint surface, a thickness of the joint surface, an anteroposterior and mediolateral bulk of each of the transverse sections of the humeral component.

3. The method according to claim 1 further comprising determining, for each of the variables, the statistical distribution according to an average value and a standard deviation, relating to the variable, in the set of statistical data.

4. The method according to claim 1, wherein each humeral component of the range has a length smaller than 100 mm.

5. The method according to claim 4 further comprising obtaining at least one reference value of a torsion torque configured to cause loosening of a humeral component installed in a proximal portion of the humerus, wherein, the measurement for each variable, for each of the sizes, is determined according to the set of statistical data and according to the at least one reference value.

6. The method according to claim 5, wherein for each of the sizes, the measurement for each of the variables, according to the set of statistical data, is determined by:
    obtaining a three-dimensional model of the humeral component including sections distributed in different planes, each section being defined by a set of geometric parameters;
    determining, for each of the sections, the set of corresponding geometrical parameters, according to the set of statistical data relating to the variables adapted to enable the characterization of the geometry of a proximal portion of the humerus; and
    determining, for each of the geometrical parameters, by means of an interpolation function, the values of the parameter between each section, wherein for each of the sections, the set of corresponding geometrical parameters can be determined according to the set of statistical data relating to the variables adapted to enable the characterization of the geometry of a proximal portion of the humerus, and according to the at least one reference value.

7. The method according to claim 6, wherein the sections have a octagonal shape, each section being provided with fillets with configurable radii, the values of the configurable radii being selected according to the at least one reference value.

8. The method according to claim 1, wherein for each of the sizes, the measurement for each of the variables, according to the set of statistical data, is determined by:
   obtaining a three-dimensional model of the humeral component including sections distributed in different planes, each section being defined by a set of geometric parameters;
   determining, for each of the sections, the set of corresponding geometrical parameters, according to the set of statistical data relating to the variables adapted to enable the characterization of the geometry of a proximal portion of the humerus; and
   determining, for each of the geometrical parameters, by means of an interpolation function, the values of the parameter between each section.

9. A system for constructing a range of humeral components intended to be introduced into a proximal portion of a humerus during a shoulder reconstruction surgery, the system comprising:
   a database including a set of statistical data relating to variables adapted to enable the characterization of the geometry of a proximal portion of the humerus, from morphometric data of proximal portions of the humerus belonging to a representative sample of a population;
   a configurator configured to:
      determine, from a statistical distribution, a set of sizes composing the range of humeral components; and
      for each of the sizes, determine a measurement for each of the variables, according to the set of statistical data; and
   a production tool configured to produce, for each of the sizes, a humeral component according to the measurement of each of the variables corresponding to the size.

10. The system according to claim 9, wherein the configurator is configured to determine, for each of the sizes, the measurement for each of the variables, according to the set of statistical data, by:
   obtaining a three-dimensional model of the humeral component including sections distributed in different planes, each section being defined by a set of geometric parameters.

11. The system according to claim 10, wherein the configurator is configured to further determine, for each of the sizes, the measurement for each of the variables, according to the set of statistical data, by:
   determining, for each of the sections, the set of corresponding geometrical parameters, according to the set of statistical data relating to the variables adapted to enable the characterization of the geometry of a proximal portion of the humerus.

12. The system according to claim 11, wherein the configurator is configured to further determine, for each of the sizes, the measurement for each of the variables, according to the set of statistical data, by:
   determining, for each of the geometrical parameters, by means of an interpolation function, the values of the parameter between each section.

13. The method according to claim 1, wherein for each of the sizes, the measurement for each of the variables, according to the set of statistical data, is determined by:
   obtaining a three-dimensional model of the humeral component including sections distributed in different planes, each section being defined by a set of geometric parameters.

14. The method according to claim 13, wherein for each of the sizes, the measurement for each of the variables, according to the set of statistical data, is further determined by:
   determining, for each of the sections, the set of corresponding geometrical parameters, according to the set of statistical data relating to the variables adapted to enable the characterization of the geometry of a proximal portion of the humerus.

15. The method according to claim 14, wherein for each of the sizes, the measurement for each of the variables, according to the set of statistical data, is further determined by:
   determining, for each of the geometrical parameters, by means of an interpolation function, the values of the parameter between each section.

* * * * *